(12) United States Patent
Matsumoto et al.

(10) Patent No.: US 8,343,060 B2
(45) Date of Patent: Jan. 1, 2013

(54) BIOLOGICAL LUMINAL BODY EVALUATING APPARATUS

(75) Inventors: Takeo Matsumoto, Nagoya (JP);
Kazuaki Nagayama, Nagoya (JP);
Kenji Takezawa, Nagoya (JP); Hiroshi Masuda, Nagoya (JP)

(73) Assignee: Unex Corporation, Nagoya (JP)

( * ) Notice: Subject to any disclaimer, the term of this patent is extended or adjusted under 35 U.S.C. 154(b) by 691 days.

(21) Appl. No.: 12/071,873

(22) Filed: Feb. 27, 2008

(65) Prior Publication Data
US 2008/0214961 A1 Sep. 4, 2008

(30) Foreign Application Priority Data

Mar. 2, 2007 (JP) .................. 2007-053508

(51) Int. Cl.
*A61B 5/02* (2006.01)
(52) U.S. Cl. .............. 600/485; 600/449; 600/500
(58) Field of Classification Search .......... 600/481–483, 600/485, 492; 128/897, 898, 900
See application file for complete search history.

(56) References Cited

U.S. PATENT DOCUMENTS

| | | | |
|---|---|---|---|
| 2003/0191399 A1* | 10/2003 | Muramatsu et al. | 600/480 |
| 2005/0070805 A1* | 3/2005 | Dafni | 600/492 |

FOREIGN PATENT DOCUMENTS

| | | |
|---|---|---|
| JP | A-10-262935 | 10/1998 |
| JP | A-2005-312745 | 11/2005 |

OTHER PUBLICATIONS

"Clinical Studies of Arterial Waves," published by Medical Review Co., Ltd., pp. 91-98, Apr. 10, 2003.
"Medical Technology," published by Ishiyaku Publishers Inc., pp. 35-40, vol. 34, No. 1, Jan. 15, 2006.
Bank et al., "In Vivo Human Brachial Artery Elastic Mechanics," *Circulation*, vol. 1, No. 41, Apr. 19, 1999.
Richter et al., "Volume Elasticity, Modulus of Elasticity and Compliance of Normal and Arteriosclerotic Human Aorta,"*Biorheology*, vol. 21, No. 5, pp. 723-734, Dec. 29, 1984.
May 15, 2012 Office Action issued in Japanese Patent Application No. 2007-053508 (w/ partial translation).

* cited by examiner

*Primary Examiner* — Charles A Marmor, II
*Assistant Examiner* — Carrie R Dorna
(74) *Attorney, Agent, or Firm* — Oliff & Berridge, PLC

(57) ABSTRACT

In a process of varying pressure of a pressure container (24) accommodating a forearm (22) of a subject (20) in a pressure range including negative pressure, a diameter (cross-sectional shape value) (D) of an artery 44 in the forearm (22) accommodated in the pressure container (24) is measured non-invasively by a vascular diameter calculating unit (76). In addition, a display controller (display controlling means) (80) operates to display on a displaying device (16) a variation of an internal pressure (Pc) in the pressure container (24) and a variation of the diameter (D) of the artery (44) varying depending thereon. Based on the diameter (D) of the artery (44) obtained in the high pressure region, the variation of the internal pressure Pc in the pressure container 24 and the variation of the diameter (D) of the artery 44 varying depending thereon i.e. mechanical properties of the artery (44) are displayed on the displaying device (16). The artery (44) can be evaluated accurately based on the mechanical properties.

8 Claims, 11 Drawing Sheets

BIOLOGICAL LUMINAL BODY EVALUATING APPARATUS

BACKGROUND OF THE INVENTION

1. Field of the Invention

The present invention relates to an biological luminal body evaluating Apparatus for evaluating a property or organ of a luminal body inside a living body.

2. Background Art

It is well known that objective measurement and evaluation of flexibility of an artery, vein, or other luminal body in a living body by non-invasive measurement are effective in some cases. They are effective upon successively or continuously evaluating, for example, a degree of progress of arteriosclerosis and for providing information for thereby applying treatment before serious symptoms occur. The serious symptoms include myocardial infarction, vascular cerebral infarction, arteriosclerosis obliterans, and aneurysm, etc.

The following methods have been known for evaluating elasticity of a vascular wall. In a first method, with a pulse wave velocity PWV (=L/DT) measured based on a time difference DT of a pulse wave between two positions along an artery separated by just a predetermined distance L, arteriosclerosis is evaluated using the pulse wave velocity PWV. In a second method, a vascular diameter Ds under a systolic blood pressure (maximum blood pressure value) Ps, and a vascular diameter Dd under a diastolic blood pressure (minimum blood pressure value) Pd are respectively measured, for example, during a single heart pulse. Thereafter, a stiffness parameter β [=In (Ps/Pd)÷(Ds−Dd)/Dd] is calculated to evaluate arteriosclerosis using it. Non-Patent Document 1 and Non-Patent Document 2 disclose such second method.

Non-Patent Document 1: "Clinical Studies of Arterial Waves," Apr. 10, 2003, published by Medical Review Co., Ltd., pp. 94-95.

Non-Patent Document 2: "Medical Technology," Jan. 15, 2006, published by Ishiyaku Publishers, Inc., pp. 35-40.

Meanwhile, in order to measure across a wider pressure range, there has been proposed a method where a measured portion of a living body is compressed using a bag filled with water, and a pressure (transmural pressure) applied to a vascular wall is defined as a difference between the pressure of compression and a blood pressure value. Elastic characteristic of the vascular wall is measured based on a variation of a vascular diameter with varying the transmural pressure. Non-Patent Document 3 discloses such blood vessel evaluating method. With this evaluating method, in accordance with a physiological pressure range or pressurization of the vascular wall during measurement, a range of an internal/external differential pressure of the vascular wall, i.e. a transmural pressure $P_A$ (=artery internal pressure−artery external pressure) is expanded as follow. It expands from a pressure range having a diastolic pressure as a lower limit value and a systolic pressure as an upper limit value, to a state in which the lower limit value is lower than the diastolic pressure. The elastic characteristics of a blood vessel can thus be known within the expanded range.

Non-Patent Document 3: In Vivo Human Brachial Artery Elastic Mechanics; Alan J. Bank et al; Circulation 1999; vol. 100; 41-47

However, the conventional method for measuring the elastic characteristics of a blood vessel has a disadvantage that the elastic characteristics of the blood vessel can be known only within the pressure range in which the upper limit value of the transmural pressure $P_A$ is the systolic pressure. In general, the elastic characteristic of the blood vessel is nonlinear. As increase of the blood pressure i.e. the transmural pressure $P_A$, the variation of the vascular diameter D relative to the blood pressure variation decreases rapidly, which appears prominently in the arteriosclerosis.

In particular, in cases of hardening of a blood vessel wall due to arteriosclerosis etc. accompanying aging, a characteristic of the variation of the vascular diameter relative to the blood pressure variation decreasing sharply in a region of comparatively high blood pressure value, is manifested. For this reason, in order to accurately know the variation of blood vessel elasticity for diagnosis and prevention, the blood vessel elastic characteristic in the high pressure region exceeding the high blood pressure value i.e. the upper limit value of the transmural pressure $P_A$ is desirably measured to be used in the diagnosis. However, the conventional method described in Non-Patent Document 3, disenabling to know the elastic characteristics in the high pressure region of transmural pressure no less than the systolic pressure, cannot not be used to know an adequate precision in regard to the elastic characteristics of a luminal body. Thus, it can not provide the adequate diagnostic precision, for example, in the arteriosclerosis.

FIG. 13 shows relationships between the transmural pressure $P_A$ and a compliance CC indicating flexibility of an artery, for a normal subject NAD, a patient I with mild arteriosclerosis, a patient II with moderate arteriosclerosis, and a patient III with severe arteriosclerosis. With the mild arteriosclerosis patient I, the compliance near 100 mHg increases once and then decreases, locally exceeding that of the normal subject NAD. The compliance decreases continuously in the high-pressure region. That is, even if the variation does not appear near 100 mmHg, it appears in the high-pressure region of 150 mmHg or more. For this reason, the conventional method can not provide the adequate diagnostic precision for arteriosclerosis.

Non-Patent Document 4: Biorheology; 1984; 21(5): 723-34. Richter H A, Mitteremayer C: Volume, elasticity, modulus of elasticity and compliance of normal and arterotic human aorta.

SUMMARY OF THE INVENTION

The present invention has been made with the above circumstances as the background, and an object thereof is to provide a biological luminal body evaluating apparatus or an evaluating apparatus for a biological luminal body which can accurately evaluate a luminal body in a living body based on its mechanical characteristic(s) or organ (s). The evaluating apparatus for the biological luminal body can be expressed in other words as an evaluation apparatus for evaluating mechanical organ (s) of a living tubular body.

To achieve the above object, a first aspect of the present invention is featured by that an biological luminal body evaluating apparatus for evaluating property of a luminal body positioned in a portion of a living body, comprising (a) a displaying device; (b) a pressure container, being varied in an internal pressure within a pressure range including a negative pressure with the portion of the living body accommodated therein; (c) a luminal body cross-sectional shape measuring device, non-invasively measuring a cross-sectional shape value of the luminal body in the portion of the living body accommodated in the pressure container; and (d) a display controlling means, displaying on the displaying device a variation of the internal pressure of the pressure container and a variation of a cross-sectional shape of the luminal body varying depending on the variation of the internal pressure of the pressure container.

A second aspect of the present invention is featured by in the first aspect that the display controlling means operates to continuously display on the displaying device a plurality of points, indicating the variation of the internal pressure of the pressure container and the variation of the cross-sectional shape of the luminal body varying depending on the variation of the internal pressure of the pressure container, in a multi-dimension coordinate system having at least the cross-sectional shape value and the pressure value in the pressure container as variables.

A third aspect of the present invention is featured by in the first or second aspect that the display controlling means operates to continuously display the internal pressure of the pressure container and the cross-sectional shape value of the luminal body along time axes.

A fourth aspect of the present invention is featured by in any of the first to third aspects further comprising a pressure controlling means, operating to vary the internal pressure of the pressure container between a minimum pressure value which is a negative pressure set in advance and a maximum pressure value which is a positive pressure set in advance to no less than a systolic pressure of the living body.

A fifth aspect of the present invention is featured by in any of the first to fourth aspects that the cross-sectional shape measuring device measures at least one value of a diameter, a luminal body wall thickness, a perimeter, and a cross-sectional area of the luminal body using an ultrasonic reflection signal inside the portion of the living body.

To achieve the above object, a sixth aspect of the present invention is featured by that an biological luminal body evaluating apparatus for evaluating property of a luminal body positioned in a portion of a living body, comprising (a) a pressure container, being varied in an internal pressure within a pressure range including a negative pressure with the portion of the living body accommodated therein; (b) a luminal body cross-sectional shape measuring device, non-invasively measuring a cross-sectional shape of the luminal body in the portion of the living body accommodated in the pressure container; (c) an evaluation value calculating means, calculating an evaluation value indicating a mechanical property of the luminal body, using a variation of the cross-sectional shape of the luminal body varying according to a variation of the internal pressure of the pressure container; and (d) an output means, outputting the evaluation value indicating the mechanical property of the luminal body, calculated by the evaluation value calculating means.

A seventh aspect of the present invention is featured by in the sixth aspect that the evaluation value calculating means calculates, as the evaluation values indicating the mechanical properties of the luminal body, an evaluation value indicating a flexibility of the luminal body and/or an evaluation value indicating a contractile ability of the luminal body, using the variation of the cross-sectional shape of the luminal body varying depending on the variation of the internal pressure of the pressure container.

A eighth aspect of the present invention is featured by in the seventh aspect that the evaluation value indicating the flexibility of the luminal body, is at least one value a stiffness parameter $\beta$, a pressure-strain modulus of elasticity Ep, an artery diameter varying rate AS, a compliance DC, a compliance CC, and an incremental modulus of elasticity $E_{inc}$; and the evaluation value, indicating a contractile ability of the luminal body, is at least one value of a vasoconstriction rate SR and a vasoconstriction time constant $\tau$.

A ninth aspect of the present invention is featured by in any of the sixth to eighth aspects that the evaluation value calculating means calculates, as the evaluation value indicating the mechanical property of the luminal body, a ratio of a value indicating a mechanical property of the luminal body obtained at a high pressure region set in advance within a varying range of a transmural pressure, relative to a value indicating the mechanical property of the luminal body obtained at a low pressure region set in advance within the varying range of the transmural pressure.

A tenth aspect of the present invention is featured by in the sixth aspect that the evaluation value calculating means calculates, as the evaluation value indicating the mechanical property of the luminal body, a ratio of an increase value of the cross-sectional shape value of the luminal body upon depressurization of the pressure container by a depressurization value set in advance, relative to a decrease value of the cross-sectional shape value of the luminal body upon pressurization of the pressure container by a pressurization value set in advance.

An eleventh aspect of the present invention is featured by in any of the sixth to tenth aspects that the cross-sectional shape measuring device measures at least one value of a diameter, a luminal body wall thickness, a perimeter, and a cross-sectional area of the luminal body based on an ultrasonic reflection signal from inside the portion of the living body.

A twelfth aspect of the present invention is featured by in any of the first to eleventh aspects that the luminal body positioned in the portion of the living body is an artery in the portion of the living body.

According to the biological luminal body evaluating apparatus of the first aspect of the present invention, the luminal body cross-sectional shape measuring device non-invasively measures the cross-sectional shape value of the luminal body in the portion of the living body, that is a living tubular body, accommodated in the pressure container. This is achieved, with the portion of the living body accommodated in the pressure container, when the internal pressure in the pressure container varies in the pressure range including negative pressure. In addition, the display controlling means operates to display on the displaying device a variation of the internal pressure of the pressure container and a variation of a cross-sectional shape of the luminal body varying depending on the variation of the internal pressure of the pressure container.

In the biological luminal body evaluating apparatus, the internal pressure of the pressure container accommodating the portion of the living body thus varies across the range including the negative pressure. The upper limit value of the transmural pressure of the luminal body which was conventionally limited to the transmural pressure corresponding to the systolic pressure thereby expands to the high pressure region adequately surpassing it. Based on the cross-sectional shape values obtained in the high pressure region, the variation of the internal pressure of the pressure container and the variation of the cross-sectional shape of the luminal body varying according thereto i.e. the mechanical properties of the luminal body, are displayed on the displaying device. The luminal body can thus be evaluated accurately based on the mechanical characteristic.

That is, in the biological luminal body evaluating apparatus, because the elastic characteristics of the luminal body can be known in the high pressure region of transmural pressure no less than the systolic pressure, and can be ascertained accurately. Thus, the adequate diagnostic precision can be obtained, for example, for the arteriosclerosis. Also, because the upper limit value of the transmural pressure of the luminal body is expanded to the high pressure region, the cross-sectional value of can be measured using the luminal body of a large diameter. Thus, both the measuring precision and evaluating precision are improved further.

According to the biological luminal body evaluating apparatus of the second aspect of the present invention, the display controlling means operates to continuously display on the displaying device the plurality of points, indicating the variation of the internal pressure of the pressure container and the variation of the cross-sectional shape of the luminal body varying depending on the variation of the internal pressure of the pressure container, in a multi-dimension coordinate system having at least the cross-sectional shape value and the pressure value in the pressure container as variables. Consequently, the mechanical properties of the luminal body can be ascertained based on the display, resulting in the accurate evaluation of the luminal body based thereon.

According to the biological luminal body evaluating apparatus of the third aspect of the present invention, the display controlling means operates to continuously display the internal pressure of the pressure container and the cross-sectional shape value of the luminal body along the time axes. Consequently, the internal pressure of the pressure container and the cross-sectional shape value of the luminal body during measurement can be ascertained to determine the measurement abnormality readily and to accommodate the abnormality rapidly.

The biological luminal body evaluating apparatus of the fourth aspect of the present invention further comprises the pressure controlling means, operating to vary the internal pressure of the pressure container between the minimum pressure value which is the negative pressure set in advance, and the maximum pressure value which is the positive pressure set in advance to no less than the systolic pressure of the living body. Consequently, by altering the setting of the minimum pressure value, the high pressure region of the transmural pressure varying range can be set to a desired range which enables the mechanical characteristic of the luminal body.

According to the biological luminal body evaluating apparatus the fifth aspect of the present invention, the cross-sectional shape measuring device measures at least one value of the diameter, the luminal body wall thickness, the perimeter, and the cross-sectional area of the luminal body using the ultrasonic reflection signal inside the portion of the living body. Consequently, the mechanical characteristic of the luminal body can be obtained accurately from the measured values.

According to the biological luminal body evaluating apparatus of the sixth aspect of the present invention, the luminal body cross-sectional shape measuring device non-invasively measures the cross-sectional shape value of the luminal body in the portion of the living body accommodated in the pressure container. This is achieved, with the portion of the living body accommodated in the pressure container, when the internal pressure in the pressure container varies in the pressure range including negative pressure. In addition, the evaluation value calculating means calculates the evaluation value indicating the mechanical property of the luminal body, using the variation of the cross-sectional shape of the luminal body varying depending on the variation of the internal pressure of the pressure container. The output means outputs the evaluation value indicating the mechanical property of the luminal body calculated by the evaluation value calculating means.

In the biological luminal body evaluating apparatus, the internal pressure of the pressure container accommodating the portion of the living body varies across the range including the negative pressure. The upper limit value of the transmural pressure of the luminal body conventionally limited to the transmural pressure corresponding to the systolic pressure expands to the high pressure region adequately surpassing it. Using on the cross-sectional shape values obtained in the high pressure region, based on the variation of the internal pressure of the pressure container and the variation of the cross-sectional shape of the luminal body varying according thereto, the evaluation value indicating the mechanical characteristic of the luminal body is calculated and output. The luininal body can thus be evaluated accurately based on the mechanical characteristic.

That is, with the biological luminal body evaluating apparatus, because the elastic characteristics of the luminal body can be known in the high pressure region of transmural pressure no less than the systolic pressure, and can be ascertained accurately. Thus, the adequate diagnostic precision can be obtained, for example, for the arteriosclerosis. Also, because the upper limit value of the transmural pressure of the luminal body expands to the high pressure region, the cross-sectional value can be measured using the luminal body of a large diameter. Thus, both the measuring precision and evaluating precision are improved further.

According to the biological luminal body evaluating apparatus of the seventh aspect of the present invention, the evaluation value calculating means calculates, as the evaluation values indicating the mechanical characteristic of the luminal body, the evaluation value indicating the flexibility of the luminal body and/or the evaluation value indicating the contractile ability of the luminal body, using the variation of the cross-sectional shape of the luminal body varying depending on the variation of the internal pressure of the pressure container. Consequently, the mechanical characteristic and functions of the luminal body can be obtained accurately based on the evaluation value indicating the flexibility of the luminal body and/or the evaluation value indicating the contractile ability of the luminal body.

According to the biological luminal body evaluating apparatus of the eighth aspect of the present invention, the evaluation value indicating the flexibility of the luminal body is at least one value of the stiffness parameter $\beta$, the pressure-strain modulus of elasticity Ep, the artery diameter varying rate AS, the compliance DC, the compliance CC, and the incremental modulus of elasticity $E_{inc}$. The evaluation value indicating a contractile ability of the luminal body, is at least one value of the vasoconstriction rate SR and the vasoconstriction time constant $\tau$. Consequently, the mechanical characteristic and function of the luminal body can thereby be obtained accurately.

According to the biological luminal body evaluating apparatus of the ninth aspect of the present invention, the evaluation value calculating means calculates, as the evaluation value indicating the mechanical property of the luminal body, the ratio of the value indicating the mechanical property of the luminal body obtained at the high pressure region set in advance within the varying range of a transmural pressure, relative to the value indicating the mechanical property of the luminal body obtained at the low pressure region set in advance within the varying range of the transmural pressure. Based on this ratio, the state of the luminal body hardening can be evaluated accurately.

According to the biological luminal body evaluating apparatus of the tenth aspect of the present invention, the evaluation value calculating means calculates following ratios, as the evaluation value indicating the mechanical property of the luminal body. The ratio is defines as the increase value of the cross-sectional shape value of the luminal body upon depressurization of the pressure container by the depressurization value set in advance, relative to the decrease value of the cross-sectional shape value of the luminal body upon pressurization of the pressure container by the pressurization value set in advance. Based on the ratio, the hardening state of the luminal body can be evaluated accurately.

According to the biological luminal body evaluating apparatus of the eleventh aspect of the present invention, the cross-sectional shape measuring device measures at least one value of the diameter, the luminal body wall thickness, the perimeter, and the cross-sectional area of the luminal body based on the ultrasonic reflection signal from inside the portion of the living body. The mechanical characteristic of the luminal body can thus be obtained accurately based on the measured values.

According to the biological luminal body evaluating apparatus of the twelfth aspect of the present invention, the luminal body positioned in the portion of the living body is the artery in the portion of the living body. Thus, the state of the artery hardening in the living body can be evaluated accurately.

Favorably, when the display controlling means operates to display the variation of the internal pressure of the pressure container and the variation of the cross-sectional shape of the luminal body varying according thereto, on the displaying device, the variation of the internal pressure of the pressure container and the variation of the cross-sectional shape of the luminal body varying according thereto can be displayed by a graph display. The variation of the internal pressure of the pressure container and the variation of the cross-sectional shape of the luminal body may also be displayed by a numerical display. For example, the numerical values indicating ratios or proportions of the variation of the internal pressure of the pressure container and the variation of the cross-sectional shape of the luminal body varying according thereto may be displayed, or variation values of the internal pressure of the pressure container and variation values of the cross-sectional shape of the luminal body may be comparatively displayed.

Favorably, the display controlling means operates to continuously display on the displaying device the plurality of points, indicating the variation of the internal pressure of the pressure container and the variation of the cross-sectional shape of the luminal body, in the two-dimensional coordinate system with the axes indicating the cross-sectional shape value and the pressure inside the pressure container. Other coordinates, such as polar coordinates expressing the cross-sectional shape value and the internal pressure the pressure container using a radius and an angle, may be used instead. In the other coordinate system, a curve containing the plurality of measured points or just the plurality of points mutually discrete may be displayed.

As the blood pressure values of the living body used for the following purposes, values measured in advance and manually input may be used. The purposes include a determination of the maximum pressure value inside the pressure container corresponding to the minimum pressure value in the varying range of transmural pressure, and the minimum pressure value inside the pressure container corresponding to the systolic pressure in the transmural pressure varying range, both used by the pressure controlling means controlling the pressure of the pressure container; and calculation of the stiffness parameter β.

Favorably, a blood pressure measuring means is provided automatically measuring the blood pressure value of the living body based on a pulse wave generated from the artery in the portion of the living body, or on an amplitude variation of a shape of the artery in the portion of the living body, with varying the compressive pressure applied to the portion of the living body. The maximum pressure value and/or the minimum pressure value inside the pressure container may be calculated automatically based on the measured values.

The maximum pressure value inside the pressure container is set, for example, to the systolic pressure of the living body. The minimum pressure value (the negative value) inside the pressure container is set to a value obtained by subtracting the systolic value from the upper limit value of the transmural pressure set in the range of approximately 200 to 250 mmHg. The diastolic pressure may be used in place of the systolic pressure.

Favorably, the cross-sectional shape value of the luminal body may be a diameter or the thickness of the luminal body, or may be a perimeter or cross-sectional area etc. of the luminal body. That is, the cross-sectional shape value can be values relating to the size of the cross-sectional shape.

Favorably, when measuring the blood pressure by the blood pressure measuring means, the portion of the living body may be compressed by a cuff, or it may be compressed by the pressure container. In this case, the pressure container is commonly used as the compressing means, so that an advantage of eliminating the cuff and a pressure controlling valve for controlling the pressure thereof, can be rendered.

The luminal body inside the living body is favorably the artery positioned inside the portion of the living body, but it may instead be another luminal body, including other circulatory organ such as a vein, other respiratory organ such as a lung, a digestive organ, or a bladder, etc. The portion of the living body is not restricted to a forearm, but may be a wrist, an upper limb portion, a femoral portion, an ankle, etc. That is, the portion may be any portion of the living body no higher than a neck.

PREFERRED EMBODIMENTS

Figure 1:
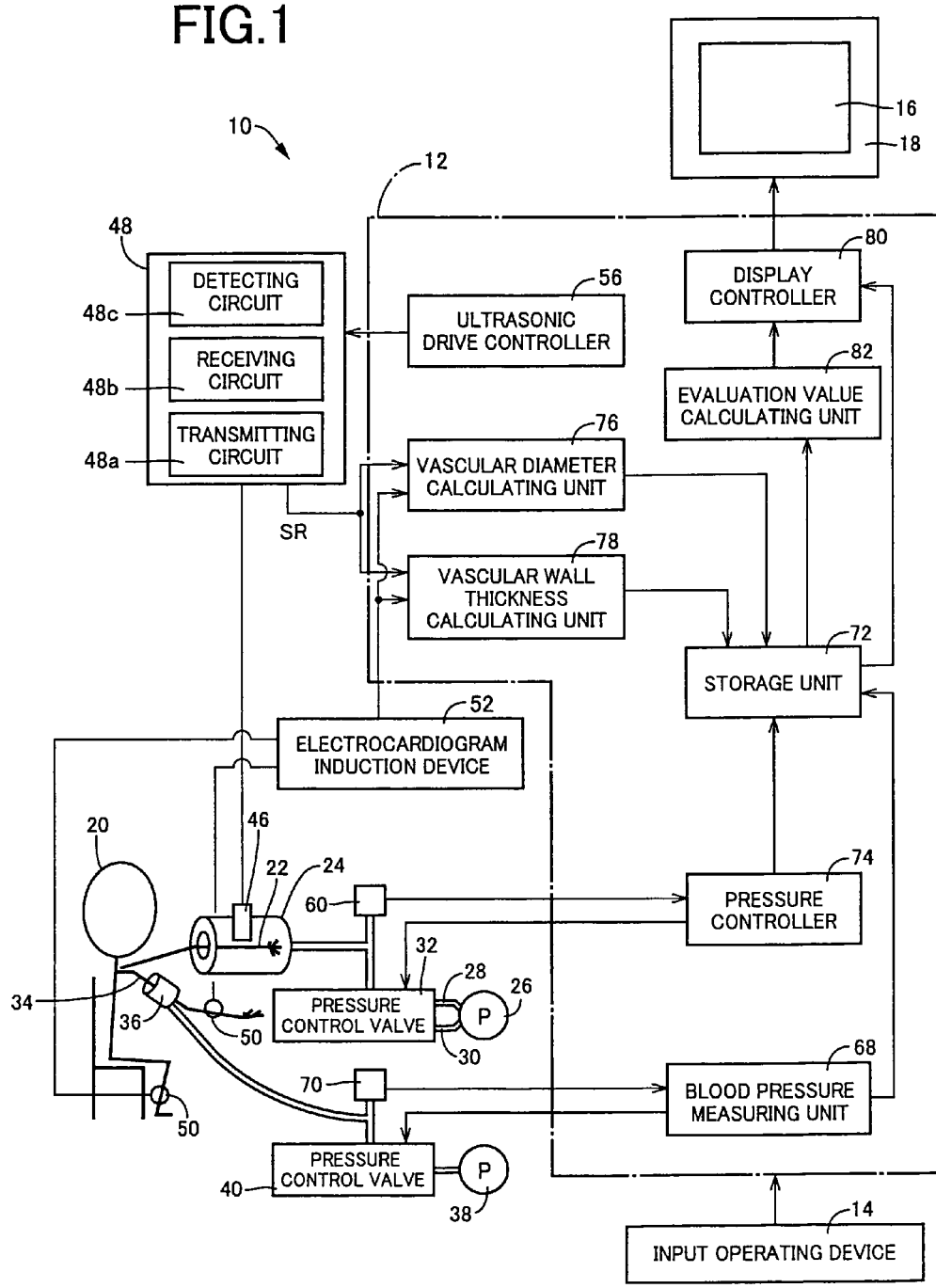
FIG. 1 is a block line diagram for describing in outline a structure of a biological luminal body evaluating apparatus according to one embodiment of the present invention.

A biological luminal body evaluating apparatus 10 according to one embodiment of the present invention shall now be described based on the drawings.
<Embodiment 1>
FIG. 1 is a block diagram for describing a structure of the biological luminal body evaluating apparatus 10. The biological luminal body evaluating apparatus 10 includes a so-called CPU, ROM, RAM, input/output interface, etc. The CPU has a main unit (electronic controlling device i.e. controller) 12, an input operating device 14, and an image displaying device 18. The main unit 12 is constituted of a microcalculater processing input signals in accordance with a program stored in advance in the ROM, etc., with using a temporary storage function of the RAM. Control functions of the main unit 12 are indicated by a plurality of blocks. The input operating device 14 is constituted of a keyboard, mouse, etc., for inputting operations signals into the main unit 12. A displaying device 16 can display a graph image, symbols, etc., according to output signals from the main unit 12.

The in-vivo-luminal body evaluating apparatus 10 includes a pressure container 24, a pressure controlling valve 32, and a pressure controlling valve 40. The pressure container 24 accommodates a forearm 22 of a subject (living body) 20 therein. The pressure controlling valve 32 selectively connects an intake path 28 and a discharge path 30 of an air pump 26 to the pressure container 24 to control a pressure inside the pressure container 24 in a pressure range from a negative pressure to a positive pressure. The pressure controlling valve 40 controls a pressure of a cuff 36 wound around an upper arm 34 of the subject (living body) 20 during blood pressure measurement, using an air pump 38 as a pressure source.

The biological luminal body evaluating apparatus 10 includes an ultrasonic probe 46, an ultrasonic drive controlling device i.e. controller 48, and an electrocardiogram induction device 52. The ultrasonic probe 46 is held by the pressure container 24 so as to contact a skin 42 of the forearm 22 and detects a cross-sectional image (cross-sectional shape) of an artery 44 immediately below the skin 42. The ultrasonic drive controller 48 operates to emit ultrasonic waves from the ultrasonic probe 46, to receive reflected waves by the ultrasonic probe 46, and to output ultrasonic reflection signals SR to the main unit 12. The electrocardiogram induction device 52 has a plurality of electrodes 50 attached to the subject 20, and outputs electrocardiogram induction signals, generated in synchronization with heart pulses of the subject to the main unit 12.

The ultrasonic probe 46 normally has a plurality of transducers (for example, piezoelectric ceramic transducers) positioned in array form along a straight line extending in a direction intersecting the artery 44. The ultrasonic drive controller 48 includes a transmitting circuit 48a, a receiving circuit 48b, and a detecting circuit 48c. The transmitting circuit 48a operates to successively drive a portion of the transducers among the plurality of transducers, and to emit ultrasonic waves therefrom. The receiving circuit 48b operates to receive reflected waves reflected from inside a living body tissue by the transducers, and to take out the reflected waves. The detecting circuit 48c detects received signals output from the receiving circuit 48b and outputs these signals to the main unit 12.

The ultrasonic drive controller 56 of the main unit 12 corresponds to a claimed ultrasonic drive control means. In every receipt of an electrocardiogram induction signal from the electrocardiogram induction device 52 in accordance with a program set in advance, the ultrasonic controller 56 performs a beam forming drive as follow. That is, the beam forming drive is performed in synchronization with the electrocardiogram induction signal at a frequency of approximately 10 MHz, with applying a predetermined phase difference according to each set of ultrasonic transducers of a fixed number of the ultrasonic probe 46, starting from an end of the plurality of ultrasonic transducer (piezoelectric ceramic) aligned in a single row constituting an ultrasonic array.

The ultrasonic drive controller 56 operates to successively emit an ultrasonic beam convergent in the direction of alignment of the ultrasonic transducers to the blood vessel 44, to receive the reflected wave of each emission, and to input the received signal into the main unit 12. On an emission surface of the ultrasonic array is disposed an acoustic lens for converging the ultrasonic beam in the direction orthogonal to the direction of alignment of the ultrasonic transducers.

Figure 2:
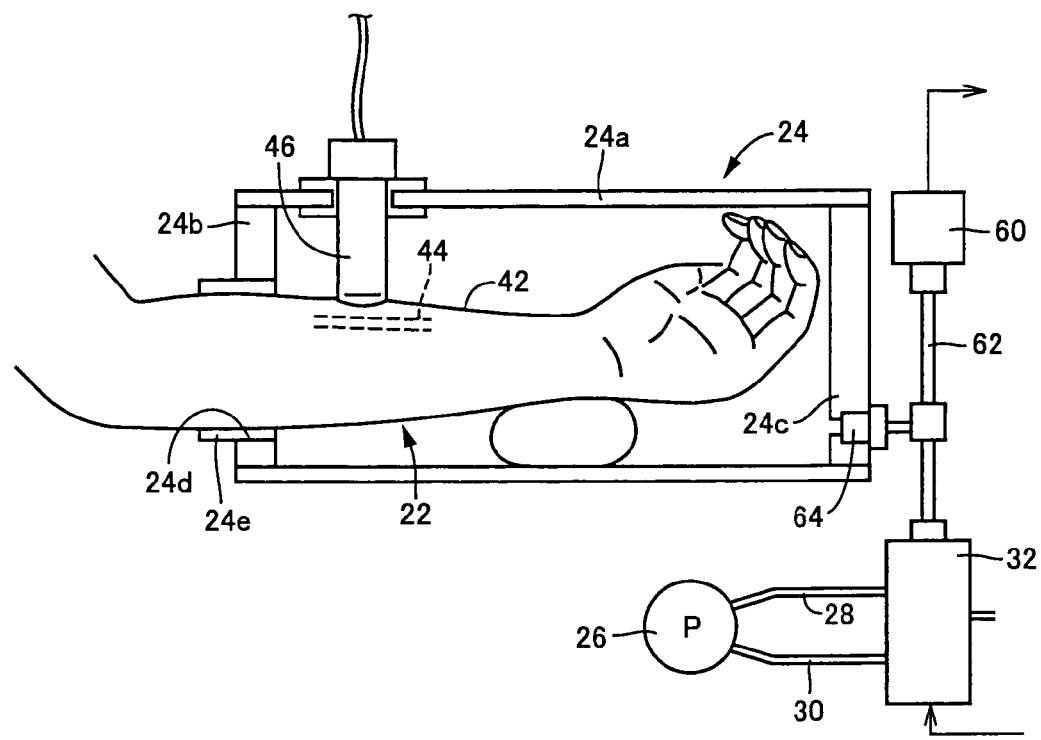
FIG. 2 is an enlarged view for describing a structure of a pressure container.

FIG. 2 shows the pressure container 24 with an enlarged scale. The pressure container 24 is constituted of a cylindrical outer circumferential wall 24a formed of a tubular member and a pair of end walls 24b and 24c closing both axial ends of the outer circumferential wall 24a in an airtight manner. One axial end wall 24b has a penetrating hole 24d for insertion of the forearm 22, and a cylindrical sealing member 24e fixed to an inner circumferential surface of the penetrating hole 24d. The sealing member 24e, formed of soft resin or synthetic rubber, maintains an interval between the penetrating hole 24d and the forearm 22.

On the other axial end wall 24c is disposed a connection socket 64 to be connected to a connecting tube 62 connected both to a pressure sensor 60 for detecting the pressure inside the pressure container 24, and to the pressure controlling valve 32. The ultrasonic probe 46 is attached to the outer peripheral wall 24a so as to contact the skin 42 of the forearm 22.

Returning now to FIG. 1, a blood pressure measuring unit 68 of the main unit 12 corresponds to a claimed blood pressure measuring means. Before measurement of mechanical characteristics of an artery and evaluation of a degree of arteriosclerosis, the cuff 36 is used to measure a blood pressure value of the subject 20 by an oscillometric method. That is, the blood measuring unit 68, for example, uses the pressure controlling valve 40 to first raise the pressure of the cuff 36 detected by a pressure sensor 70 to a hemostatic pressure higher than a systolic pressure (maximum blood pressure value) of the subject 20, and thereafter gradually lowers the pressure at a predetermined pressure lowering rate. In this process, pressure vibration waves generated in synchronization with heart pulses due to the pressure of the cuff 36, that is pulse waves, are extracted. The pressures of the cuff 36 corresponding to inflection points of an envelope curve joining amplitudes of the pulse waves, that is, corresponding to maximum values of pulse amplitude differential, are determined as a systolic pressure Ps and a diastolic pressure Pd, being stored in a storage unit 72.

A pressure controlling unit i.e. controller 74 of the main unit 12 corresponds to a claimed pressure controlling means. In measuring the mechanical characteristic of an artery and evaluating the degree of arteriosclerosis, the pressure Pc inside the pressure container 24 is varied reciprocatingly in a varying range including negative pressure, for example, from a lower limit value of zero to an upper limit value of approximately 200 to 250 mmHg. Here, the varying range including negative pressure means a varying range corresponding to a varying range of an internal/external differential pressure across a vascular wall of the artery, that is, a transmural pressure $P_A$ (=artery internal pressure−artery external pressure).

The measurement of the variation of the cross-sectional shape of the artery 44 is rationally performed between a state where the cross-sectional shape can be measured to be the smallest, and a state where the cross-sectional shape can be measured to be the largest. Thus, when the artery internal pressure is the diastolic pressure Pd, the pressure controller 74 sets the pressure Pc in the pressure container 24 to its maximum pressure value of the diastolic pressure Pd, and sets the transmural pressure $P_A$ to the lower limit value of 0 mmHg.

When the artery internal pressure is the systolic pressure Ps, the pressure controller 74 sets the pressure Pc in the pressure container 24 to its minimum pressure value, for example, of the negative value of approximately −80 mmHg, and varies the transmural pressure $P_A$ to the upper limit value of approximately 200 to 250 mmHg. The minimum pressure value (negative value) inside the pressure container 24 is determined to be the value obtained by subtracting, from the systolic pressure Ps, the upper limit value of the transmural pressure $P_A$ set in advance. As the diastolic pressure Pd and the systolic pressure Ps, those measured by the blood pressure measuring unit 68 and stored in the storage unit 72 are employed. However, in absence of the blood pressure measuring unit 68, blood pressure values measured separately are manually input.

A vascular diameter calculating unit 76 of the main unit 12 corresponds to a claimed vascular diameter calculating means. The vascular diameter calculating unit 76 receives the ultrasonic reflection signals SR through a gate opening in every receipt of an electrocardiogram induction signal from the electrocardiogram induction device 52, and processes the ultrasonic reflection signals SR in synchronization thereto. The vascular diameter calculating unit 76 calculates repeatedly the vascular diameter D (mm) of the artery 44, and successively stores it in the storage unit 72 together with both the pressure Pc in the pressure container 24 and the transmural pressure $P_A$ upon measurement.

In a diameter direction of the artery 44, there exists a vascular wall at a side close to the ultrasonic probe 46 and a vascular wall at a side away from the probe 46. A first reflection wave from the closer vascular wall and a second reflection wave from the farther vascular wall are included in the ultrasonic reflection signals SR. Thus, the vascular diameter calculating unit 76 calculates, for example, the outer diameter (vascular diameter) D of the artery 44 based on a time difference between a leading end of the first reflection wave and a trail end of the second reflection wave, and a propagation velocity in the living tissue set in advance. Also, a cross-sectional image of the artery 44 is generated using the ultrasonic reflection signals SR, based on which the vascular diameter D of the artery 44 is determined 44.

A vascular wall thickness calculating unit 78 of the main unit 12 corresponds to a claimed vascular wall thickness calculating means. The vascular wall thickness calculating unit 78 receives the ultrasonic reflection signals SR through the gate opening in every receipt of an electrocardiogram induction signal from the electrocardiogram induction device 52, and processes them. The vascular wall thickness calculating unit 78 calculates repeatedly the vascular wall thickness T (mm) of the artery 44, and successively stores it in the storage unit 72 together with both the pressure Pc in the pressure container 24 and the transmural pressure $P_A$ upon measurement.

The vascular wall thickness calculating unit 78 calculates the vascular wall thickness T of the artery 44 based, for example, on the time difference, between the leading end and the trail end of the first reflection wave or between the leading end and the trail end of the second reflection wave, and the propagation velocity in the living tissue set in advance. For example, the vascular wall thickness calculating unit 78 determines the outer diameter D and an inner cavity diameter d of the artery 44 based on an ultrasonic image or the time difference between the first reflection wave, and calculates the second reflection wave and the vascular wall thickness T (=(D−d)/2) of the artery 44 based on these differences.

When the electrocardiogram induction device 52 is not used, the following manner can be employed. That is, ultrasonic waves are emitted and received repeatedly at a frequency of no less than 10 times/second. A maximum value for the vascular wall diameter D is set to an artery diameter Ds at the systolic pressure, and a minimum value for the vascular wall diameter D is set to an artery diameter Dd at the diastolic pressure. A maximum value for the vascular wall thickness T is set to a vascular wall thickness Ts at the systolic pressure, and a minimum value for the vascular wall thickness T is set to a vascular wall thickness Td at the diastolic pressure.

A display controller 80 of the main unit 12 corresponds to a claimed display controlling means. During measurement in which the pressure Pc inside the pressure container 24 is varied by the pressure controller 74, the display controlling unit i.e. controller 80 successively displays on the displaying device 16, for example, numerical values indicating the pressure Pc inside the pressure container 24 and the vascular diameter D and vascular wall thickness T of the artery 44, and a trend graph, indicating variations of these numerical values relative to the time. In this process, the vascular diameter D and the vascular wall thickness T of the artery 44 stored in the storage unit 72 together with the pressure Pc in the pressure container 24 and the transmural pressure $P_A$ during measurement are used.

When the pressure Pc inside the pressure container 24 is varied reciprocatingly in the varying range including negative pressure by the pressure controller 74, the display controller 80 performs the following display based on the pressure Pc inside the pressure container 24, the vascular diameter D and vascular wall thickness T of the artery 44 all measured and successively stored in the storage unit 72 during this reciprocating variation. As mentioned above, the varying range including negative pressure means the range with which the internal/external differential pressure across the vascular wall of the artery 44, that is, the transmural pressure $P_A$ (=artery internal pressure−artery external pressure) is varied from the lower limit value for example of zero, to the upper limit value of approximately 200 to 250 mmHg.

Figure 4:
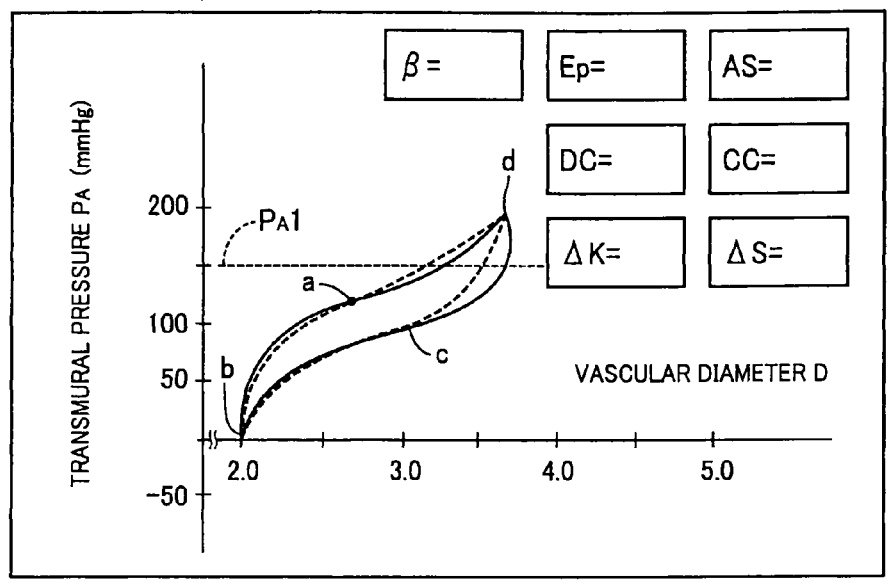
FIG. 4 is a diagram of a display example of a graph indicating a relationship of an artery diameter and a transmural pressure, that is, a mechanical property of the artery displayed by the display controller of FIG. 1 upon completion of measurement.
Figure 5:
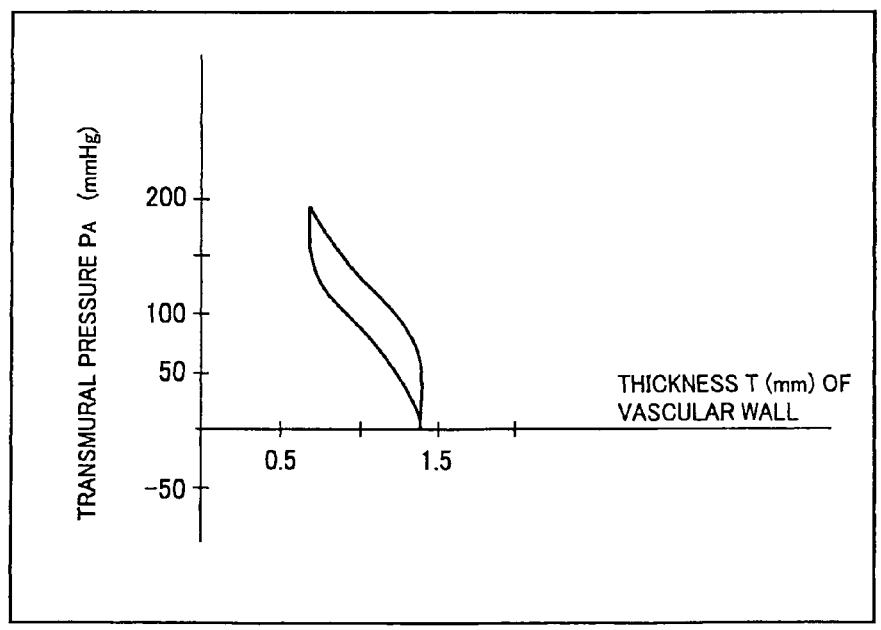
FIG. 5 is a diagram of a display example of a graph indicating a relationship of an artery wall thickness and the transmural pressure, that is, a mechanical property of the artery displayed by the display controller of FIG. 1 upon completion of measurement.
Figure 6:
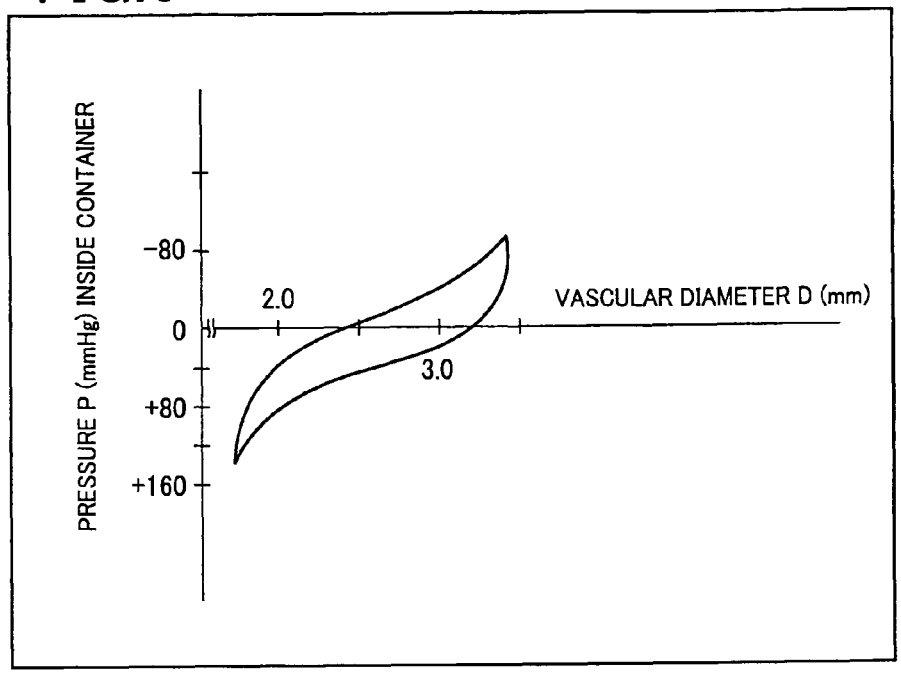
FIG. 6 is a diagram of a display example of a graph indicating a relationship of the artery diameter and a pressure container internal pressure, that is, a mechanical property of the artery displayed by the display controller of FIG. 1 upon completion of measurement.
Figure 7:
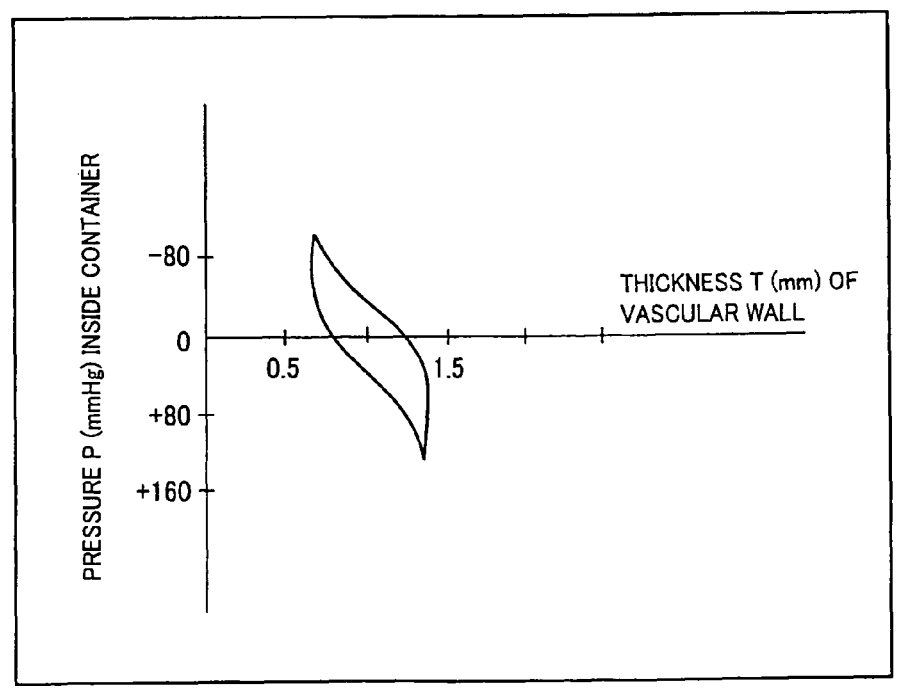
FIG. 7 is a diagram of a display example of a graph indicating a relationship of the artery wall thickness and the pressure container internal pressure, that is, a mechanical property of the artery displayed by the display controller of FIG. 1 upon completion of measurement.

Following graphs are displayed as the display, as shown in FIG. 7, at once or displayed selectively in accordance with a manual selection operation. The graphs include a graph indicating a variation of the vascular diameter D relative to the transmural pressure $P_A$ as shown in FIG. 4, a graph indicating a variation of the vascular wall thickness T relative to the transmural pressure $P_A$ as shown in FIG. 5, a graph indicating a variation of the vascular diameter D relative to the pressure Pc inside the pressure container 24 as shown in FIG. 6, and a graph indicating a variation of the vascular wall thickness T relative to the pressure Pc inside the pressure container 24 as shown in FIG. 7. In these graphs, data plots are converted by interpolation to a continuous curve, but plots of discrete data may be displayed as they are. Such graphs indicate the mechanical characteristic relevant to the flexibility or hardness of the artery 44, being used to evaluate the hardness degree of the artery 44.

For example in FIG. 4, a broken line curve indicates the mechanical characteristic of the artery of the normal subject, and a solid line curve indicates the mechanical characteristics of the artery of the arteriosclerosis patient. In the high pressure region in the range of the transmural pressure $P_A$ of 120 to 200 mmHg, the transmural pressure $P_A$ of the solid line curve increases steeply relative to the vascular diameter D, which means the artery 44 is hard. In contrast, in the broken line curve, the increase of the transmural pressure $P_A$ relative to the increase of the vascular diameter D is relatively gradual, which means the artery 44 is comparatively flexible. The vascular diameter D is normalized in both the broken line curve and the solid line curve in FIG. 4.

An evaluation value calculating unit 82 of the main unit 12 corresponds to a claimed evaluation value calculating means. When the pressure Pc inside the pressure container 24 is reciprocatingly varied in the varying range including negative pressure by the pressure controller 74, the evaluation value calculating unit 82 performs following calculations, for example, in the high pressure region of 120 to 150 mmHg and higher, of the varying range of the transmural pressure $P_A$. As the varying range, the pressure controller 74 varies the internal/external differential pressure across the vascular wall of the artery 44, that is, the transmural pressure $P_A$ (=artery internal pressure−artery external pressure) from the lower limit value for example of zero to the upper limit value of approximately 200 to 250 mmHg.

In detail, the evaluation value calculating unit 82 calculates the values indicating the mechanical properties of the artery 44, that is, values for evaluating the state of hardening of the artery 44 calculated using formulae (1) to (7) shown below, to thereby calculate a time constant τ during vasoconstriction. As the values for evaluating the state of hardening, for example, a stiffness parameter β, a pressure-strain modulus of elasticity Ep, an artery diameter varying rate AS, a compliance DC, a compliance CC, an incremental modulus of elasticity $E_{inc}$, and a vasoconstriction rate SR are used.

In the following formulae (1) to (7), Ps represents the systolic pressure, Pd represents the diastolic pressure, Ds represents the maximum vascular diameter of the artery, Dd represents the minimum vascular diameter of the artery, ΔD represents a variation of vascular diameter, ΔP represents a variation of blood pressure value, and ln represents a natural logarithm. In formula (6), $D_0$ represents an outer diameter of a blood vessel, $D_1$ represents an inner diameter of the blood vessel, and ν represents a Poisson's ratio. In formula (7), $ΔD_2$ represents an increase amount of the diameter of the artery 44 under the negative pressure of the pressure Pc inside the pressure container 24, and $ΔD_1$ represents a decrease amount of the diameter upon elapse of a predetermined time thereafter.

$$\beta = \ln(Ps/Pd) \div (Ds-Dd)/Dd \tag{1}$$

$$Ep = (Ps-Pd)/[(Ds-Dd)/Dd] \tag{2}$$

$$AS = (Ds-Dd)/Dd \tag{3}$$

$$DC = (2\Delta D/D)/\Delta P \tag{4}$$

$$CC = \pi D(\Delta D/2\Delta P) \tag{5}$$

$$E_{inc} = \Delta P \cdot 2(1-\nu^2)D_0 D_1^2 / \Delta \cdot D(D_0^2 - D_1^2) \tag{6}$$

$$SR = \Delta D_2 / \Delta D_1 \tag{7}$$

Figure 14:
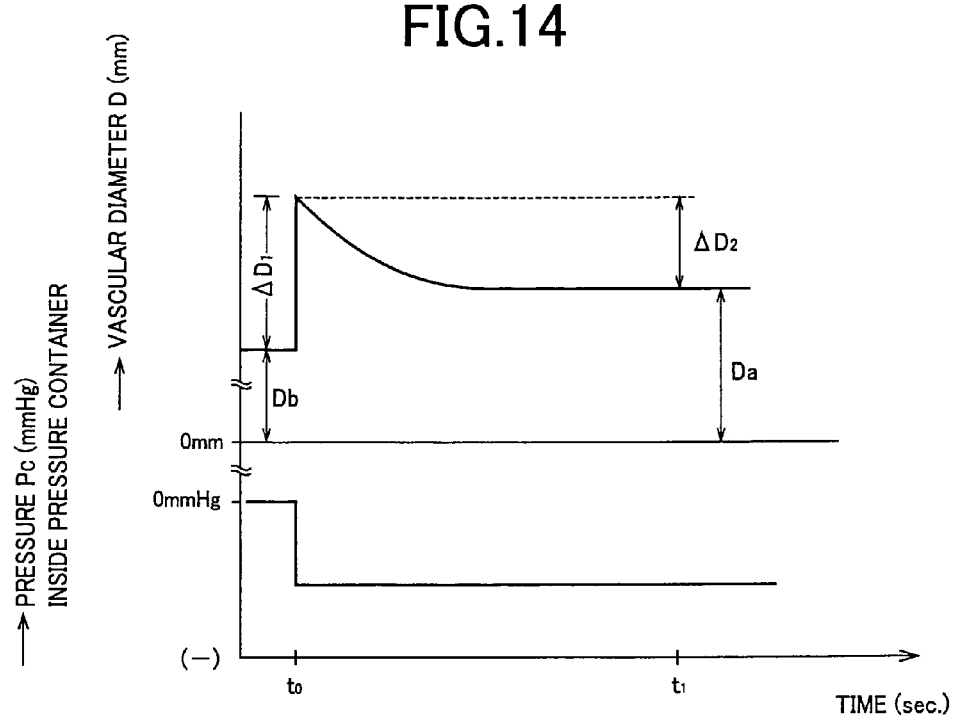
FIG. 14 is a logarithmic curve showing how, in a negative pressure of the pressure container, an artery diameter of a subject in the pressure container increases once and thereafter decreases.

FIG. 14 shows a phenomenon of increase of the diameter D of the artery 44 occurring with the pressure Pc inside the pressure container 24 set to a negative pressure, and a subsequent decrease of the diameter D along a logarithmic curve due to actions of a smooth muscle. This phenomenon is referred to as a Bayliss effect or Myogenic theory. The vasoconstriction rate SR indicates a contractile ability of the smooth muscle related to a health state (arteriosclerotic state) of the blood vessel. For example, the vasoconstriction time constant τ corresponds to an elapsed time at which the pressure Pc in the pressure container 24 is made negative in FIG. 14, and it is determined by measurement of time at which the decrease curve of the vascular diameter reaches $0.368 \times \Delta D_2$.

The evaluation value calculating unit 82 calculates the following values as values indicating mechanical properties of the artery 44. The calculated values are the respective differences of the stiffness parameter β, the pressure-strain modulus of elasticity Ep, the artery diameter varying rate AS, the expansion factor DC or the compliance factor CC, the incremental modulus of elasticity $E_{inc}$, the vasoconstriction rate SR, and the vasoconstriction time constant τ in the high pressure region of for example 120 to 150 mmHg and higher in the varying range of transmural pressure $P_A$, from that of in a low pressure region of for example 80 mmHg or less in the varying range of transmural pressure $P_A$.

Also, the calculated values are the respective ratios ΔK of the stiffness parameter β, the pressure-strain modulus of elasticity Ep, the artery diameter varying rate AS, the expansion factor DC or the compliance factor CC, the incremental modulus of elasticity $E_{inc}$, the vasoconstriction rate SR, and the vasoconstriction time constant τ in a low pressure region of, for example, 80 mmHg or less in the varying range of transmural pressure $P_A$, relative to that of in a low pressure region of for example 80 mmHg or less in the varying range of transmural pressure $P_A$.

The evaluation value calculating unit 82 calculates, as the value indicating the mechanical property of the artery 44, a ratio ΔS of an increase amount $ΔD^+$ of the vascular diameter D in the high-pressure region upon pressure decrease in the pressure container 24 by just a depressurization value set in advance, relative to a decrease amount $\Delta D^-$ of the vascular diameter D upon pressure increase in the pressure container 24 by just a pressurization value set in advance.

The pressure controller 74 reciprocatingly varies the pressure Pc inside the pressure container 24 in the varying range including negative pressure. The varying range including negative pressure means a range which varies the internal/external differential pressure across the vascular wall of the artery 44, that is, the transmural pressure $P_A$ (=artery internal pressure−artery external pressure), from the lower limit value for example of zero to the upper limit value of approximately 200 to 250 mmHg.

In this process, the display controller 80 displays, as shown in FIG. 4, on the displaying device 16 the stiffness parameter β, the pressure-strain modulus of elasticity Ep, the artery diameter varying rate AS, the expansion factor DC, the compliance factor CC, the incremental modulus of elasticity $E_{inc}$, the vasoconstriction rate SR, and the vasoconstriction time constant τ, or the ratios ΔK and/of the ratio ΔS of these values and. In this process, data are used, which is set at a predetermined transmural pressure $P_A1$ of, for example, 150 mmHg in advance as indicating the high pressure region.

Figure 8:
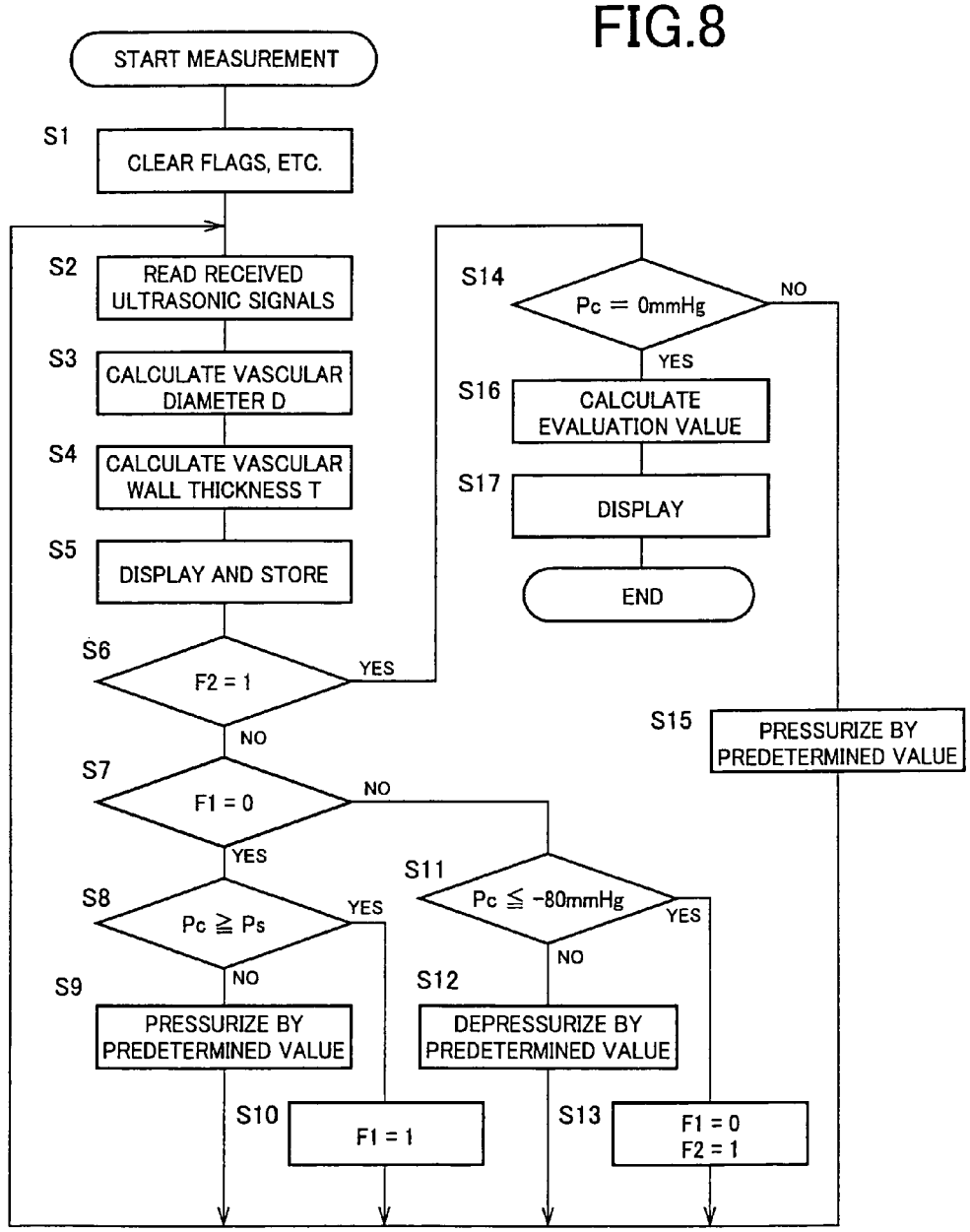
FIG. 8 is a flowchart for describing principal portions of control operation of a main unit of the biological luminal body evaluating apparatus of FIG. 1.

FIG. 8 is a flowchart for describing control operation for the vascular mechanical characteristic measurement of the main unit 12 which is the electronic controller. This sequence starts by a starting input operation performed with the forearm 22 of the subject 20 accommodated in the pressure container 24, the ultrasonic probe 46 is attached to be positioned on the artery 44 which for example is a radial artery in the forearm 22.

In FIG. 8, after flags etc. are cleared in step S1 (hereinafter, the term "step" shall be omitted), the ultrasonic reflection signals SR are read in S2. Then, in S3 corresponding to the vascular diameter-calculating unit 7, with the ultrasonic reflection signals SR processed, the diameter D (mm) of the artery 44 immediately below the ultrasonic probe 46 is calculated and stored in the storage unit 72.

Figure 3:
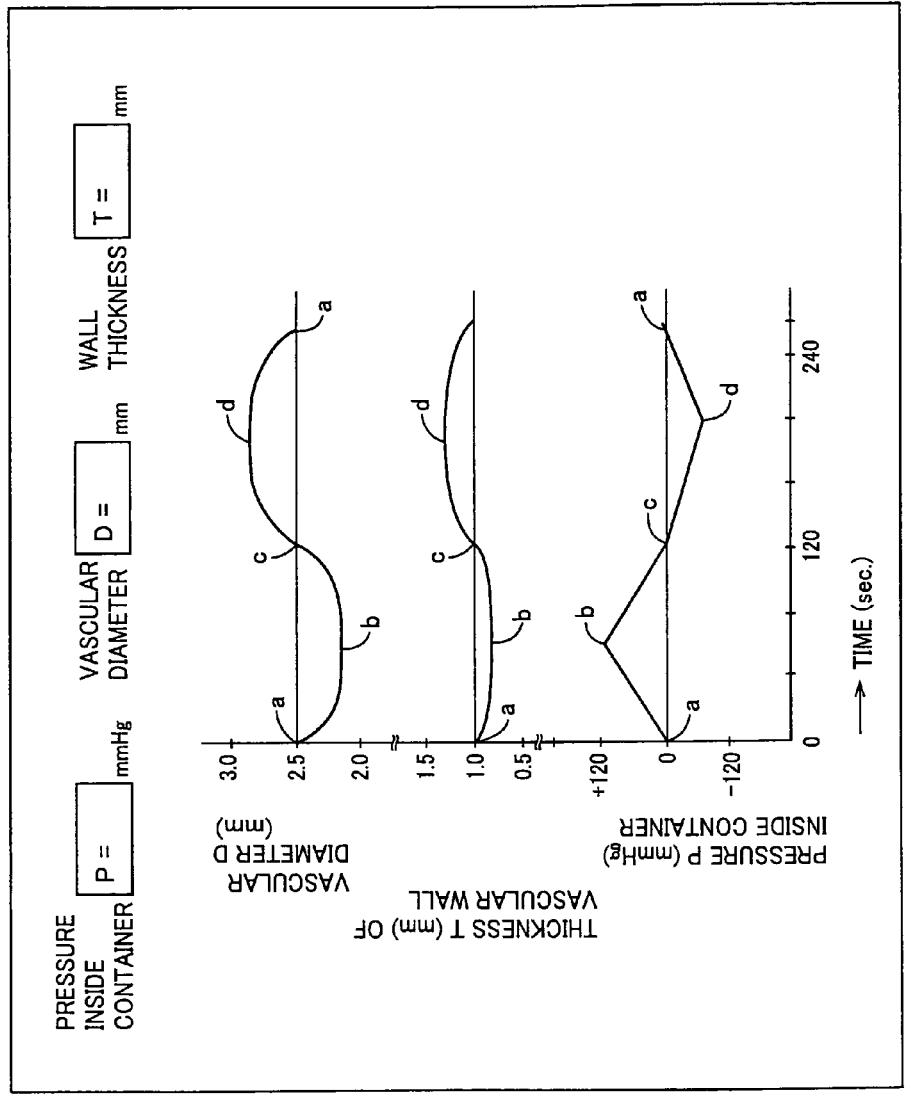
FIG. 3 is a diagram of a display example of a diameter and a wall thickness of an artery successively displayed by the display controller of FIG. 1 during measurement.

Then, in S4 corresponding to the vascular wall thickness calculating unit 78, the ultrasonic reflection signal SR is processed to calculate the wall thickness T (mm) of the artery 44 immediately below the ultrasonic probe 46 calculated for thereby storing it in the storage unit 72. In S5 corresponding to the display controller 80, the calculated diameter D and wall thickness T of the artery 44, together with the current pressure Pc inside the pressure container 24 as shown in FIG. 3, are numerically displayed and graphically displayed along time axes.

In S6, whether or not the pressure Pc inside the pressure container 24 is 0 mmHg (the transmural pressure $P_A$ is the systolic pressure Ps) and a re-depressurization elapse flag F2 is set to "1" are judged. A negative judgment is initially made in S6. In S7, whether or not a re-pressurization elapse flag F1 is reset to "0" is judged. Because of an initial positive judgment made in S7, S8 judges whether or not the pressure Pc in the pressure container 24 is no less than the systolic pressure Ps (the transmural pressure is no more than 0 mmHg) which is the upper limit value of the pressure Pc.

Because of an initial negative judgment made in S8, the pressure Pc in the pressure container 24 is raised in S9 corresponding to the pressure controller 74, by just a predetermined pressurization value ΔPc1 set in advance, for example, in a range of approximately 1 to 20 mmHg. When the pressurization value ΔPc1 is set to approximately 1 mmHg, the pressurization is performed in a continuous manner, and when the pressurization value ΔPc1 is set in a range of approximately 10 to 20 mmHg, the pressurization is performed in a step-like manner. With repeated execution of the control cycle including S2 and steps subsequent thereto, the diameter D and the wall thickness T of the artery 44 are calculated repeatedly while the pressure Pc in the pressure container 24 is raised successively. Respective intervals from "a", to b in FIG. 3 and FIG. 4 indicate this state.

While the above-described control cycle is executed repeatedly, the pressure Pc in the pressure container 24 reaches the systolic pressure Ps (the transmural pressure $P_A$ becomes 0 mmHg). Then, a positive judgment is made in S8, so that the re-pressurization elapse flag F1 is set to "1" in S10. In the next control cycle including S2 and steps subsequent thereto, a negative judgment is made in S7. In S11, whether or not the pressure Pc in the pressure container 24 becomes no more than −80 mmHg which is the lower limit value of the pressure Pc is judged. That is, whether the transmural pressure becomes no less than its maximum value (Ps+80 mmHg) which for example is 200 mmHg is judged.

A negative judgment is initially made in S11. Thus, in S12 corresponding to the pressure controller 74, the pressure Pc in the pressure container 24 is reduced by just a predetermined depressurization value ΔPc2 set in advance, for example, in a range of approximately-1 to-20 mmHg. Then, with repeated execution of the control cycle including S2 and steps subsequent thereto, the diameter D and the wall thickness T of the artery 44 are calculated repeatedly while the pressure Pc in the pressure container 24 is reduced successively. Respective intervals from b to d via c in FIG. 3 and FIG. 4 indicate this state.

While the above-described control cycle is executed repeatedly, the pressure Pc in the pressure container 24 reaches the lower limit value of −80 mmHg (the transmural pressure $P_A$ reaches its maximum value (Ps+80 mHg)), so that a positive judgment is made in S11. The re-pressurization elapse flag F1 is set to "0", and the re-depressurization elapse flag F2 is set to "1", as shown in S13. Respective intervals from d to "a" in FIG. 3 and FIG. 4 indicate this state.

Thus, in the control cycle including S2 and steps subsequent thereto, a positive judgment is made in S6. Then, in S14 whether or not the pressure Pc in the pressure container 24 reaches its starting value of 0 mmHg (atmospheric pressure) is judged. A negative judgment is initially made in S14. Thus, in S15 corresponding to the pressure controller 74, the pressure Pc in the pressure container 24 is increased by just the predetermined pressurization value ΔPc1 set in advance in a range for example of approximately 1 to 20 mmHg. With the control cycle including S2 and steps subsequent thereto executed repeatedly, the diameter D and the wall thickness T of the artery 44 are calculated repeatedly while the pressure Pc in the pressure container 24 is increased successively. Respective intervals from d to "a" in FIG. 3 and FIG. 4 indicate this state.

While the above-described control cycle is executed repeatedly, the pressure Pc in the pressure container 24 reaches the starting pressure of 0 mmHg, so that a positive judgment is made in S14. Thus, in S16 corresponding to the evaluation value calculating unit 82, the stiffness parameter β, the pressure-strain modulus of elasticity Ep, the artery diameter varying rate AS, the expansion factor DC, the compliance factor CC, the incremental modulus of elasticity $E_{inc}$, the vasoconstriction rate SR, the vasoconstriction time constant τ, and the ratios ΔK and/or the ratio ΔS of these are calculated.

In S17 corresponding to the display controller 80, the evaluation values calculated in S16 are displayed on the displaying device 16. In addition, based on the data stored in the storage unit 72 following graphs are displayed on the displaying device 16 as shown in FIG. 7. The displayed graphs include the graph indicating the variation of the vascular diameter D relative to the transmural pressure $P_A$ as shown in FIG. 4, the graph indicating the variation of the vascular wall thickness T relative to the transmural pressure $P_A$ as shown in FIG. 5, the graph indicating the variation of the vascular diameter D relative to the pressure Pc inside the pressure container 24 as shown in FIG. 6, and the graph indicating the variation of the vascular wall thickness T relative to the pressure Pc inside the pressure container 24 are displayed. These graphs are displayed all at once or are displayed selectively in accordance with a manual selection operation As mentioned above, according to the biological luminal body evaluating apparatus 10 of the present embodiment, with the forearm 22 of the subject 20 accommodated in the pressure container 24, the vascular diameter calculating unit (cross-sectional shape measuring device) 76 can non-invasively measure the diameter (cross-sectional shape value) D of the artery 44 in the forearm 22 accommodated in the pressure container 24. This measurement is performed during the process of varying the internal pressure of the pressure container 24 in the pressure range including negative pressure. In addition, the display controller (display controlling means) 80 operates to display the variation of the internal pressure Pc in the pressure container 24 and the variation of the diameter D of the artery 44 in accordance therewith on the displaying device 16.

Thus, the interior of the pressure container 24 accommodating the forearm 22 varies in the pressure range including negative pressure. The upper limit value of the transmural pressure $P_A$ of the artery 44 conventionally limited to the transmural pressure corresponding to the systolic pressure can be expanded to the high pressure region adequately surpassing it, of approximately 200 mmHg. Based on the diameter D of the artery 44 obtained in the high pressure region, the variation of the internal pressure Pc in the pressure container 24 and the variation of the diameter D of the artery 44 varying according thereto, that is, the mechanical characteristic of the artery 44 are displayed on the displaying device 16. Consequently, the artery 44 can be evaluated accurately based on the mechanical characteristic.

That is, because the elastic characteristics of the artery 44 can be known in the high pressure region of the transmural pressure $P_A$ of no less than the systolic pressure, and can be ascertained accurately, the adequate diagnostic precision can be obtained, even for the arteriosclerosis. Also, because the upper limit value of the transmural pressure $P_A$ of the artery 44 can be expanded to the high pressure region, the mechanical characteristics can be measured and evaluated with the large diameter of the artery 44. Thus, both the measuring precision and evaluating precision are improved further.

Figure 9:
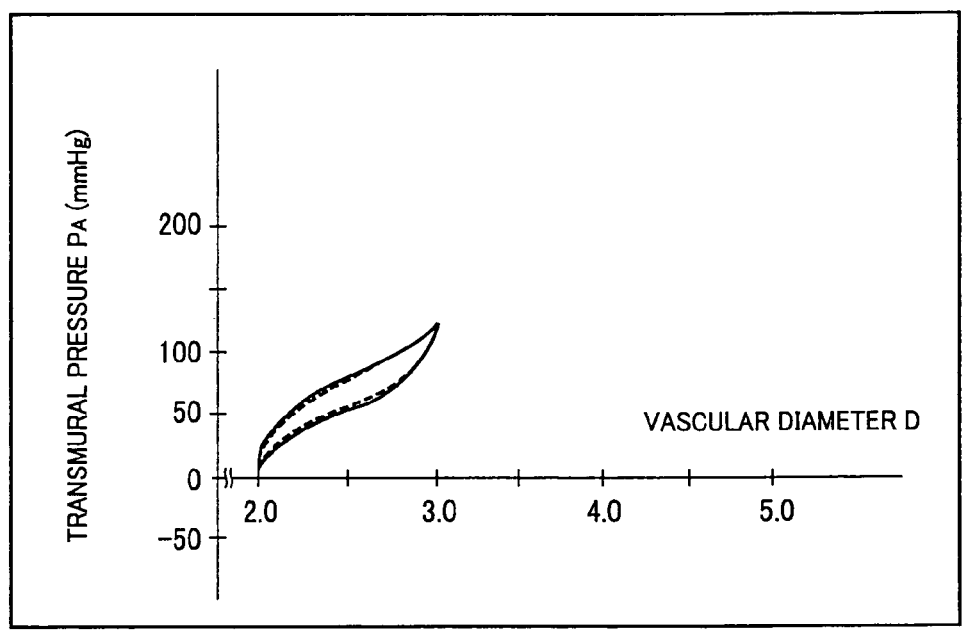
FIG. 9 is a diagram showing a relationship between a variation of a diameter D of an artery and a variation of a tranmural pressure $P_A$. The artery diameter D varies in accordance with the variation of the compressive pressure applied to the artery when a measured portion of the living body is compressed by a bag filled with water. The transmural pressure applied to the blood vessel wall is defined as a difference between the compressive pressure and the blood pressure value. The elastic characteristic of the blood vessel wall is measured based on the variation of the vascular diameter with the applied pressure varied.

FIG. 9 shows a variation of the diameter D of the artery 44 varying depending on the variation of the compressive pressure applied to the artery 44 similar to FIG. 4. Here, the conventional apparatus is used in which the measured portion of the living body is compressed using the bag filled with water, the pressure (transmural pressure) applied to the vascular wall is defined as the difference between the compressive pressure and the blood pressure value, and the elastic characteristic of the vascular wall are measured based on the variation of the vascular diameter with varying the transmural pressure.

In this case, because the upper limit value of the transmural pressure $P_A$ cannot exceed the systolic pressure Ps, the evaluating apparatus can measure the pressure in the high pressure region near 200 mmHg. The arteriosclerosis patient indicated by a solid line and the normal subject indicated by the broken line can not be distinguished from each other, resulting in the inadequate measurement and evaluation precisions. As in FIG. 4, the vascular diameter D is normalized in FIG. 9 as well.

According to the biological luminal body evaluating apparatus 10 of the present embodiment, the display controller (display controlling means) 80 operates to continuously display on the displaying device 16 the plurality of points, in the two-dimensional coordinate system having the axis indicating the diameter (cross-sectional shape value) D of the artery 44 and the axis indicating the pressure Pc inside the pressure container 24. The plurality of points include the points indicating the variation of the internal pressure Pc in the pressure container 24 and the variation of the diameter (cross-sectional shape value) D of the artery 44 varying according thereto. Consequently, by ascertaining the mechanical properties of the artery 44 based on the display, the artery 44 can be evaluated accurately based on the mechanical properties.

According to the biological luminal body evaluating apparatus 10 of the present embodiment, the display controller (display controlling means) 80 operates to continuously display the internal pressure Pc in the pressure container 24 and the diameter (cross-sectional shape value) D of the artery 44 along the time axes. By ascertaining the internal pressure Pc in the pressure container 24 and the diameter D of the artery 44 during measurement, the measurement abnormality can be determined readily and the abnormality can be accommodated rapidly.

The display controller (display controlling means) 80 of the biological luminal body evaluating apparatus 10 according to the present embodiment operates to vary the internal pressure Pc in the pressure container 24 between the minimum pressure value (of, for example, −80 mmHg) which is the negative pressure set in advance, and the maximum pressure value (of, for example, 200 mmHg) which is the positive pressure set in advance to no less than the systolic pressure Ps of the subject 20. By changing the setting of the minimum pressure value, the high pressure region in the varying range of the transmural pressure $P_A$ of the artery 44 can be set to the desired range in the high pressure region in which the mechanical properties of the artery 44 can be measured.

According to the biological luminal body evaluating apparatus 10 of the present embodiment, the vascular diameter calculating unit (cross-sectional shape measuring device) 76 measures the diameter D and the vascular wall thickness T of the artery 44 based on the ultrasonic reflection signals SR within the forearm 22 of the subject 20. Consequently, the mechanical properties of the artery 44 can be acquired accurately based on the measured values.

According to the biological luminal body evaluating apparatus 10 of the present embodiment, with the forearm 22 of the subject 20 accommodated in the pressure container 24, the diameter D and the wall thickness T of the artery 44 in the forearm 22 of the subject 20 accommodated in the pressure container 24 are measured non-invasively, by the vascular diameter calculating unit 76 and the vascular wall thickness calculating unit (cross-sectional shape measuring device) 78. The measurements are performed during the process of varying the internal pressure Pc in the pressure container 24 in the pressure range including negative pressure. In addition, the evaluation value calculating unit (evaluation value calculating means) 82 calculates the evaluation values indicating the mechanical properties of the artery 44 based on the variation of the diameter D of the artery 44 varying depending on the variation of the internal pressure Pc in the pressure container 24. The display controller (output means) 80 operates to output the evaluation values indicating the mechanical characteristic of the artery 44 calculated by the evaluation value calculating unit 82.

The interior of the pressure container 24 accommodating the forearm 22 of the subject 20 varies in the pressure range including negative pressure. Thus, the upper limit value of the transmural pressure $P_A$ of the artery 44 conventionally limited to the transmural pressure corresponding to the systolic pressure expands to the high pressure region adequately surpassing it, of approximately 200 mmHg. Based on the variation of the internal pressure Pc in the pressure container 24 and the variation of the diameter D of the artery 44 varying according thereto, using the cross-sectional shape values obtained in the high pressure region, the evaluation values indicating the mechanical properties of the artery 44 are calculated and output. Thus, the artery 44 can be evaluated accurately based on the mechanical characteristic.

That is, the elastic characteristics of transmural pressure $P_A$ can be known in the high pressure region no less than the systolic pressure, and can be ascertained with good precision, so that an adequate diagnostic precision can be obtained, for example, for the arteriosclerosis. Also, with the upper limit value of the transmural pressure of the artery 44 expanded to the high pressure region, the artery 44 can be measured and evaluated with the large diameter D. Thus, both the measuring precision and evaluating precision are improved further.

According to the biological luminal body evaluating apparatus 10 of the present embodiment, the evaluation value calculating unit 82 calculates, based on the variation of the diameter D of the artery varying depending on the variation of the internal pressure Pc in the pressure container 24, at least one of the following values as the evaluation value indicating the mechanical property of the artery 44. These values include the stiffness parameter β, the pressure-strain modulus of elasticity Ep, the artery diameter varying rate AS, the expansion factor DC, the compliance factor CC, the incremental modulus of elasticity $E_{inc}$, the vasoconstriction rate SR, and the vasoconstriction time constant τ. The mechanical characteristic of the artery 44 can be obtained accurately based on these calculated values.

According to the biological luminal body evaluating apparatus 10 of the present embodiment, the evaluation value calculating unit 82 calculates, as the evaluation values indicating mechanical characteristic of the artery 44, the differences or ratios ΔK of the evaluation values indicated below. The values are the evaluating value indicating the mechanical properties of the artery 44 obtained in the high pressure region of, for example, 120 to 150 mmHg and higher set in advance within the varying range of transmural pressure $P_A$, and that obtained in a low pressure region of, for example, 80 mmHg or less set in advance within the varying range of transmural pressure $P_A$. The evaluating values include the stiffness parameter β, the pressure-strain modulus of elasticity Ep, the artery diameter varying rate AS, the expansion factor DC or the compliance factor CC, the incremental modulus of elasticity $E_{inc}$, the vasoconstriction rate SR, and the vasoconstriction time constant τ. The state of hardening of the artery 44 can be evaluated accurately based on the differences or ratios ΔK of these evaluating values.

According to the biological luminal body evaluating apparatus 10 of the present embodiment, the evaluation value calculating unit 82 calculates, as the evaluation value indicating the mechanical property of the artery 44, the ratio ΔS of the increase amount $\Delta D^+$ of the diameter D of the artery 44 upon pressure decrease of the pressure container 24 by just the depressurization value set in advance, relative to the decrease amount $\Delta D^-$ of the diameter D of the artery 44 upon pressure increase of the pressure container 24 by just the pressurization value set in advance. The state of hardening of the artery 44 can be evaluated accurately based on the ratio ΔS.

According to the biological luminal body evaluating apparatus 10 of the present embodiment, the vascular diameter calculating unit (cross-sectional shape measuring device) 76 measures the diameter D of the artery 44 based on the ultrasonic reflection signals SR obtained inside the forearm 22 of the subject 20. The mechanical properties of the artery 44 can be acquired accurately based on the measured diameter D of the artery 44.

<Embodiment 2>

A biological luminal body evaluating apparatus 90 according to another embodiment of the present invention shall now be described. In the following description, portions in common to the above Embodiment 1 shall be provided with the same symbols, and description thereof shall be omitted.

Figure 10:
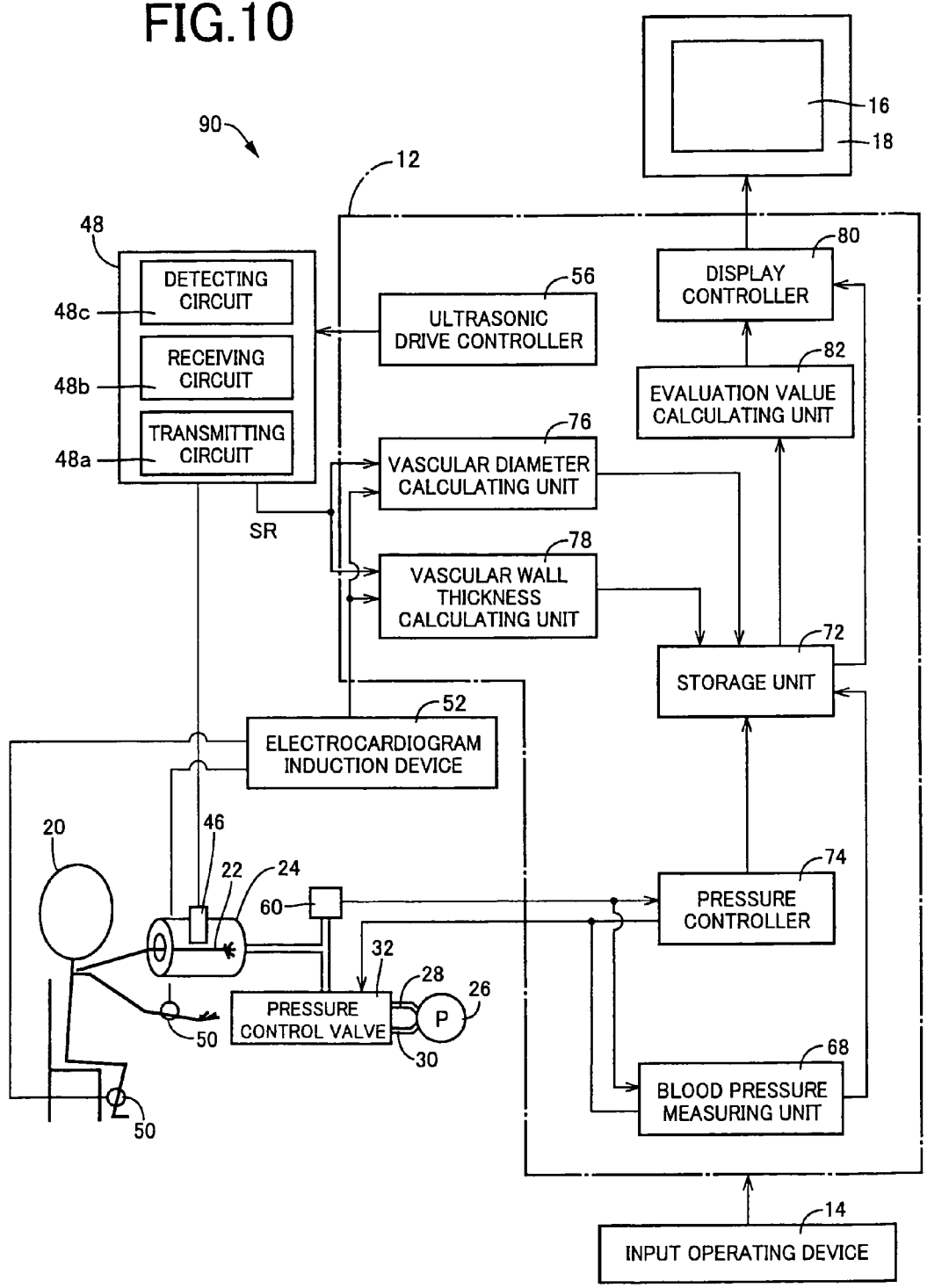
FIG. 10 is a block line diagram for describing in outline a structure of a biological luminal body evaluating apparatus according to another embodiment of the present invention.

As shown in FIG. 10, the biological luminal body evaluating apparatus 90 differs from the above-described biological luminal body evaluating apparatus 10 in that a blood pressure measuring unit 68 uses the pressure container 24 in place of the cuff 36 during blood pressure measurement. Other portions of the apparatus are constructed in the same manner as the Embodiment 1.

Figure 11:
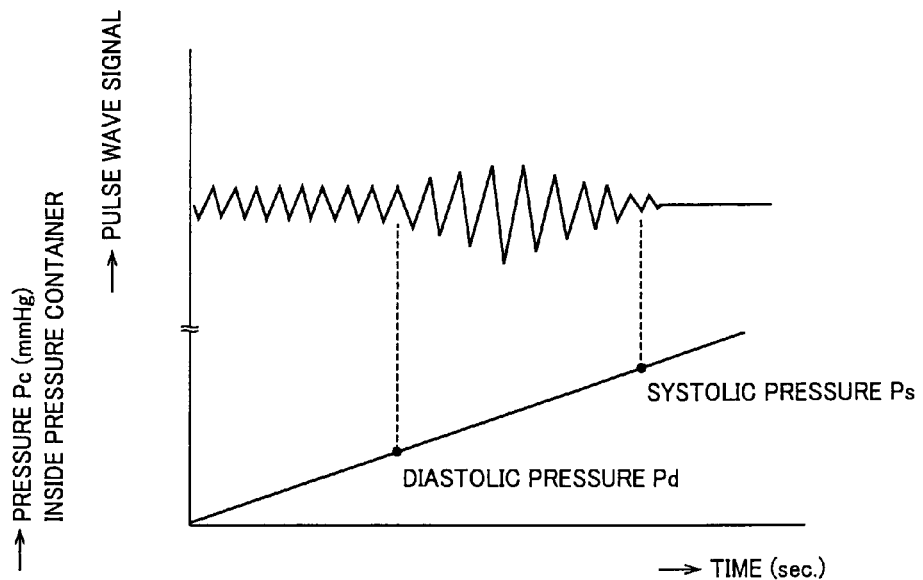
FIG. 11 is a time chart for describing a blood pressure measuring operation using a pressure container of a blood pressure measuring unit provided in the biological luminal body evaluating apparatus according to the embodiment of FIG. 10.

As shown, for example, in FIG. 11, in the gradually raising process of the pressure Pc in the pressure container 24 to a pressure higher than the systolic pressure by a predetermined value at a predetermined rate, the blood pressure measuring unit 68 determines the pressure Pc in the pressure container 24 at predetermined timing as the diastolic pressure and the systolic pressure. The predetermined timing is a timing at which the amplitude differential (variation amount rate) of the pulse wave which is the pressure vibration contained in the pressure Pc in the pressure container 24, is maximized.

Figure 12:
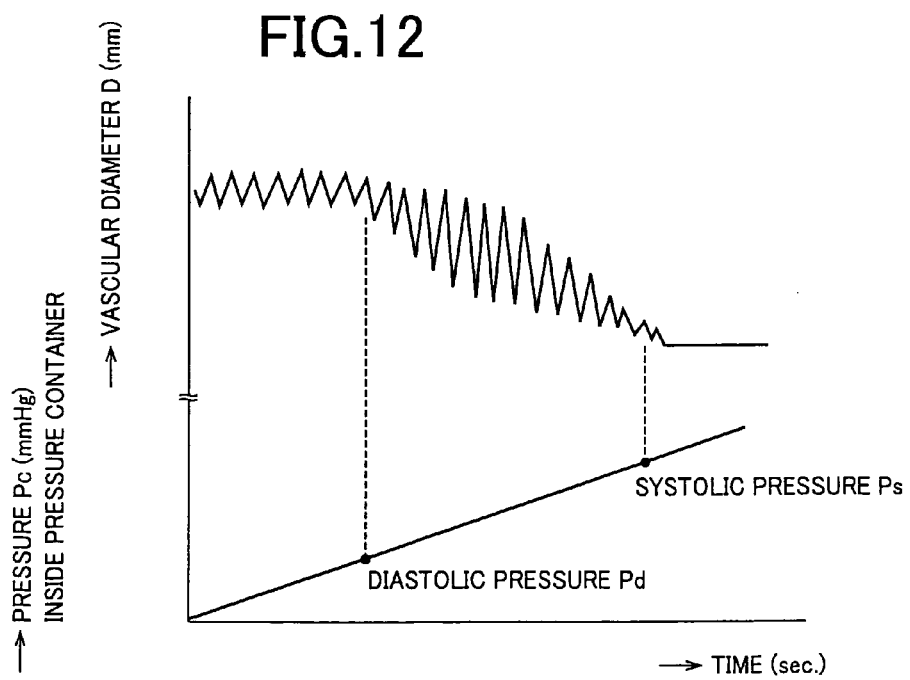
FIG. 12 is a time chart for describing another blood pressure measuring operation using the pressure container of the blood pressure measuring unit provided in the biological luminal body evaluating apparatus according to the embodiment of FIG. 10.
Figure 13:
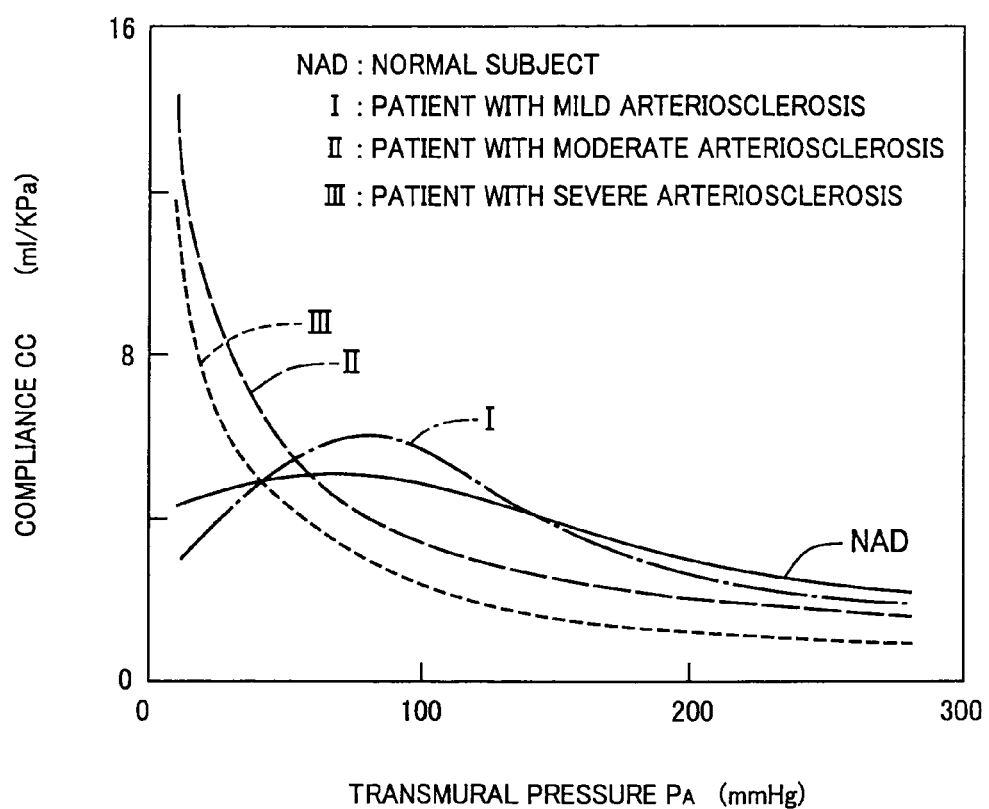
FIG. 13 is a diagram of relationships of compliance of an artery and the transmural pressure for a normal subject, a patient with mild arteriosclerosis, a patient with moderate arteriosclerosis, and a patient with severe arteriosclerosis.

As shown in FIG. 12, in the gradually raising process of the pressure Pc in the pressure container 24 to the pressure higher than the systolic pressure by the predetermined value at the predetermined rate, the blood pressure measuring unit 68 determines the pressures Pc in the pressure container 24, at the timing at which the differential of the amplitude of the diameter D of the artery 44 is maximized, as the diastolic pressure and the systolic pressure.

According to the biological luminal body evaluating apparatus 90 of the present Embodiment 2, the same effects as that of the biological luminal body evaluating apparatus 10 according to the above-described Embodiment 1 are obtained. In addition, there are advantages that the cuff 36, the pressure controlling valve 40, etc., are used specifically for the blood pressure measurement can be eliminated, and a % FMD based on the varying rate of the vascular diameter D is measured.

Described above are merely embodiments of the present invention. The present invention can be carried out in various modes in which modifications and improvements are added based on the knowledge of those skilled in the art.

What is claimed is:

1. A biological luminal body evaluating apparatus for evaluating a luminal body positioned in a portion of a living body, comprising:
   a displaying device;
   a pressure container, having an accommodation space for accommodating the portion of the living body therein, an internal pressure of the accommodation space being varied within a pressure range including a negative pressure, and the portion of the living body being exposed to the negative pressure in the accommodation space;

a luminal body cross-sectional shape measuring device that non-invasively measures a cross-sectional shape value of the luminal body in the portion of the living body accommodated in the accommodation space; and a display controller that displays on the displaying device a variation of the internal pressure in the accommodation space of the pressure container and a variation of a cross-sectional shape of the luminal body varying depending on the variation of the internal pressure of the accommodation space.

2. The biological luminal body evaluating apparatus according to claim 1, wherein the display controller operates to continuously display on the displaying device a plurality of points, indicating the variation of the internal pressure of the accommodation space and the variation of the cross-sectional shape of the luminal body varying depending on the variation of the internal pressure of the accommodation space, in a multi-dimension coordinate system having at least the cross-sectional shape value and the pressure value in the pressure container as variables.

3. The biological luminal body evaluating apparatus according to claim 1, wherein the display controller operates to continuously display the internal pressure of the accommodation space and the cross-sectional shape value of the luminal body along time axes.

4. The biological luminal body evaluating apparatus according to claim 2, wherein the display controller operates to continuously display the internal pressure of the accommodation space and the cross-sectional shape value of the luminal body along time axes.

5. The biological luminal body evaluating apparatus according to claim 1, further comprising a pressure controller that operates to vary the internal pressure of the accommodation space between a minimum pressure value which is a negative pressure set in advance and a maximum pressure value which is a positive pressure set in advance to no less than a systolic pressure of the living body.

6. The biological luminal body evaluating apparatus according to claim 1, wherein the cross-sectional shape measuring device measures at least one value of a diameter, a luminal body wall thickness, a perimeter, and a cross-sectional area of the luminal body by detecting an ultrasonic reflection signal inside the portion of the living body.

7. The biological luminal body evaluating apparatus according to claim 1, wherein the cross-sectional shape measuring device measures a cross-sectional shape value of an artery in the portion of the living body.

8. The biological luminal body evaluating apparatus according to claim 1, wherein the negative pressure in the accommodation space ranges from 0 mmHg to −80 mmHg.

* * * * *